United States Patent [19]

Bundy

[11] 4,127,569

[45] Nov. 28, 1978

[54] 9-DEOXY-9-METHYLENE-PGF$_1$-HEXAMETHYLIMINOAMIDES

[75] Inventor: Gordon L. Bundy, Portage, Mich.

[73] Assignee: The Upjohn Company, Kalamazoo, Mich.

[21] Appl. No.: 894,216

[22] Filed: Apr. 7, 1978

Related U.S. Application Data

[63] Continuation-in-part of Ser. No. 786,250, Apr. 11, 1977, Pat. No. 4,098,805.

[51] Int. Cl.$^2$ .......................................... C07C 177/00
[52] U.S. Cl. .......................... 260/239 BF; 260/239 B
[58] Field of Search .................... 260/239 BF, 239 B

[56] References Cited

PUBLICATIONS

Derwent Abstract, 16389 U.B NL 7211860-Q, 05-03-73.
Derwent Abstract, 75530x/40, U.S. 3981868, 21-09-76/

*Primary Examiner*—Paul J. Killos
*Attorney, Agent, or Firm*—Robert A. Armitage

[57] ABSTRACT

The present invention relates to novel 9-deoxy-9-methylene-PGF$_1$-hexamethyliminoamides. These compounds are useful pharmacological agents, and are useful for the same purposes as the corresponding 9-deoxy-9-methylene-PGF-type acids.

32 Claims, No Drawings

9-DEOXY-9-METHYLENE-PGF$_1$-HEXAMETHYLIMINOAMIDES

CROSS REFERENCE TO RELATED APPLICATIONS

This application is a continuation-in-part of Ser. No. 786,250, filed April 11, 1977, now U.S. Pat. No. 4,098,805, issued July 4, 1978.

The present invention relates to novel 9-deoxy-9-methylene-PGF$_1$-hexamethyliminoamides, the essential material constituting a disclosure of which is incorporated here by reference from U.S. Pat. No. 4,098,805.

I claim:

1. A prostaglandin analog of the formula

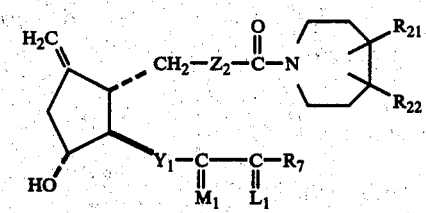

wherein Y$_1$ is trans—CH=CH—, —C≡C—, or —CH$_2$CH$_2$— wherein M$_1$ is

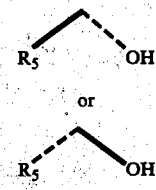

wherein
R$_5$ is hydrogen or methyl;
wherein L$_1$ is

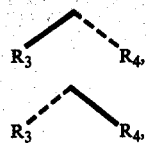

or a mixture of

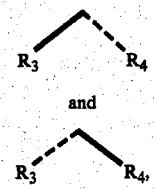

wherein R$_3$ and R$_4$ are hydrogen, methyl, or fluoro, being the same or different, with the proviso that one of R$_3$ and R$_4$ is fluoro only when the other is hydrogen or fluoro;

wherein Z$_2$ is

—(CH$_2$)$_3$—(CH$_2$)$_g$—CH$_2$—, (1)

—(CH$_2$)$_3$—(CH$_2$)$_g$—CF$_2$—, (2)

—CH$_2$—O—CH$_2$—(CH$_2$)$_g$—CH$_2$—, (3)

—C=C—CH$_2$—(CH$_2$)$_g$—CH$_2$—, (4)

—CH$_2$—C=C—(CH$_2$)$_g$—CH$_2$—, (5)

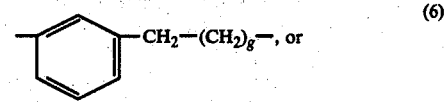

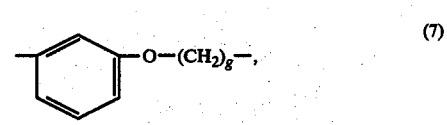

wherein g is one, 2 or 3;
wherein R$_7$ is

—(CH$_2$)$_m$—CH$_3$, (1)

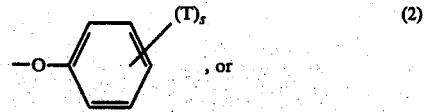

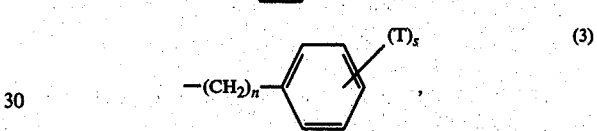

wherein m is one to 5, inclusive, h is zero or one, T is chloro, fluoro, trifluromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that R$_7$ is

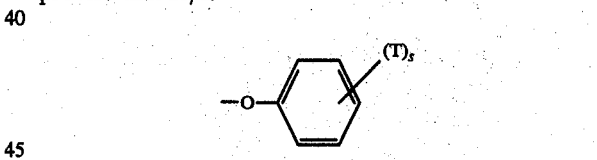

wherein T and s are as defined above, only when R$_3$ and R$_4$ are hydrogen or methyl, being the same or different; and wherein R$_{21}$ and R$_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive.

2. A prostaglandin analog according to claim 1, wherein Y$_1$ is —C≡C—.

3. 9-Deoxy-9-methylene-13,14-didehydro-PGF$_1$, hexamethyliminoamide, a prostaglandin analog according to claim 2.

4. A prostaglandin analog according to claim 1, wherein Y$_1$ is —CH$_2$CH$_2$—.

5. 9-Deoxy-9-methylene-13,14-dihydro-PGF$_1$, hexamethyliminoamide, a prostaglandin analog according to claim 4.

6. A prostaglandin analog according to claim 1, wherein Y$_1$ is trans—CH=CH—.

7. A prostaglandin analog according to claim 6, wherein $Z_2$ is aromatic.

8. 9-Deoxy-9-methylene-3,7-inter-m-phenylene-3-oxa-4,5,6-trinor-PGF$_1$, hexamethyliminoamide, a prostaglandin analog according to claim 7.

9. 9-Deoxy-9-methylene-3,7-inter-m-phenylene-4,5,6-trinor-PGF$_1$, hexamethyliminoamide, a prostaglandin analog according to claim 7.

10. A prostaglandin analog according to claim 6, wherein $Z_2$ is aliphatic.

11. A prostaglandin analog according to claim 10, wherein $M_1$ is

12. 15-epi-9-deoxy-9-methylene-PGF$_1$, hexamethyliminoamide, a prostaglandin analog according to claim 11.

13. A prostaglandin analog according to claim 10, wherein $M_1$ is

14. A prostaglandin analog according to claim 13, wherein $Z_2$ is cis—CH=CH—CH$_2$—(CH$_2$)$_g$—CH$_2$—.

15. A prostaglandin analog according to claim 14, wherein $R_7$ is

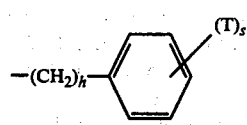

16. 9-Deoxy-9-methylene-17-phenyl-18,19,20-trinor-PGF$_1$, hexamethyliminoamide a prostaglandin analog according to claim 15.

17. A prostaglandin analog according to claim 14, wherein $R_7$ is

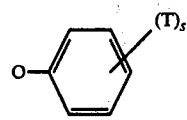

18. 9-Deoxy-9-methylene-16-phenoxy-17,18,19,20-tetranor-PGF$_1$, hexamethyliminoamide, a prostaglandin analog according to claim 17.

19. A prostaglandin analog according to claim 14, wherein $R_7$ is —(CH$_2$)$_m$—CH$_3$.

20. A prostaglandin analog according to claim 19, wherein m is 3.

21. A prostaglandin analog according to claim 20, wherein g is 3.

22. 2a,2b-Dihomo-9-deoxy-9-methylene-15-methyl-PGF$_1$, hexamethyliminoamide, a prostaglandin analog according to claim 21.

23. A prostaglandin analog according to claim 20, wherein g is one.

24. A prostaglandin analog according to claim 23, wherein at least one of $R_3$ and $R_4$ is methyl.

25. 9-Deoxy-9-methylene-16,16-dimethyl-PGF$_1$, hexamethyliminoamide, a prostaglandin analog according to claim 24.

26. A prostaglandin analog according to claim 23, wherein at least one of $R_3$ and $R_4$ is fluoro.

27. 9-Deoxy-9-methylene-16,16-difluoro-PGF$_1$, hexamethyliminoamide, a prostaglandin analog according to claim 26.

28. A prostaglandin analog according to claim 23, wherein $R_3$ and $R_4$ are both hydrogen.

29. A prostaglandin analog according to claim 28, wherein $R_5$ is methyl.

30. 9-Deoxy-9-methylene-15-methyl-PGF$_1$, hexamethyliminoamide, a prostaglandin analog according to claim 29.

31. A prostaglandin analog according to claim 28, wherein $R_5$ is hydrogen.

32. 9-Deoxy-9-methylene-PGF$_1$, hexamethyliminoamide, a prostaglandin analog according to claim 31.

* * * * *

UNITED STATES PATENT OFFICE
CERTIFICATE OF CORRECTION

Patent No. 4,127,569     Dated November 28, 1978

Inventor(s) Gordon L. Bundy

It is certified that error appears in the above-identified patent and that said Letters Patent are hereby corrected as shown below:

Column 2, lines 28-31,

"  " should read -- 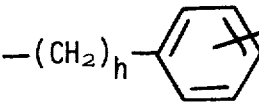 --

Signed and Sealed this

Tenth Day of July 1979

[SEAL]

Attest:

LUTRELLE F. PARKER
Attesting Officer    Acting Commissioner of Patents and Trademarks